United States Patent [19]

Jahnig

[11] 4,185,332
[45] Jan. 29, 1980

[54] BREAST FORM HOLDER

[76] Inventor: Dorothy S. Jahnig, 14900 SW. 80th Ave., Miami, Fla. 33158

[21] Appl. No.: 907,555

[22] Filed: May 19, 1978

[51] Int. Cl.² ............................................. A41C 3/10
[52] U.S. Cl. ........................................ 3/36; 128/478; 128/479; 128/482; 128/515
[58] Field of Search ...................... 3/36; 128/478, 479, 128/480, 481, 482, 486, 507, 508, 513, 514, 515, 491

[56] References Cited

U.S. PATENT DOCUMENTS

| | | | |
|---|---|---|---|
| 1,417,930 | 5/1922 | Mailleue | 3/36 |
| 1,849,514 | 3/1932 | Edelmann | 128/515 |
| 1,882,023 | 10/1932 | Malnick | 128/491 |
| 2,258,209 | 10/1941 | De Jorio | 128/478 X |
| 2,421,561 | 6/1947 | Hunau | 128/478 |
| 2,486,836 | 11/1949 | Garson | 128/515 |
| 2,779,943 | 2/1957 | Kelleher | 3/36 |
| 3,322,127 | 5/1967 | Sachs | 128/491 X |
| 3,401,407 | 9/1968 | Pittman | 3/36 |
| 3,498,297 | 3/1970 | Lord | 3/36 X |
| 3,568,681 | 3/1971 | Comollo | 128/481 X |
| 3,950,792 | 4/1976 | Williams | 3/36 |

FOREIGN PATENT DOCUMENTS

| | | | |
|---|---|---|---|
| 1406005 | 6/1965 | France | 3/36 |
| 2294657 | 7/1976 | France | 128/479 |

*Primary Examiner*—Clifford D. Crowder
*Attorney, Agent, or Firm*—Oltman and Flynn

[57] ABSTRACT

The present invention, to be worn over a woman's amputated breast, has generally triangular back and front fabric panels which provide between them a pocket for holding a breast form. The panels have adhering fabric strips along one side for closing an opening leading into the pocket between them. The front panel is of soft, flexible, thin, stretchable material, such as knitted tricot "Spandex" or jersey fabric, so that the breast form holder closely simulates an unsupported natural breast when the breast form is in the pocket.

4 Claims, 3 Drawing Figures

U.S. Patent
Jan. 29, 1980
4,185,332
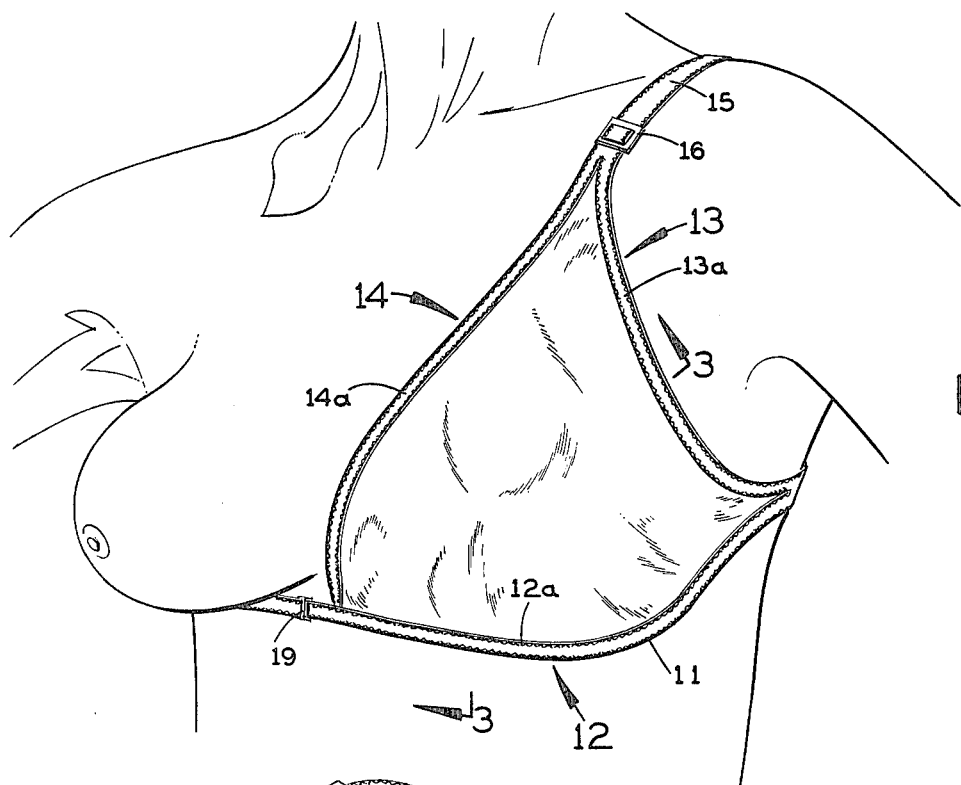
FIG. 1
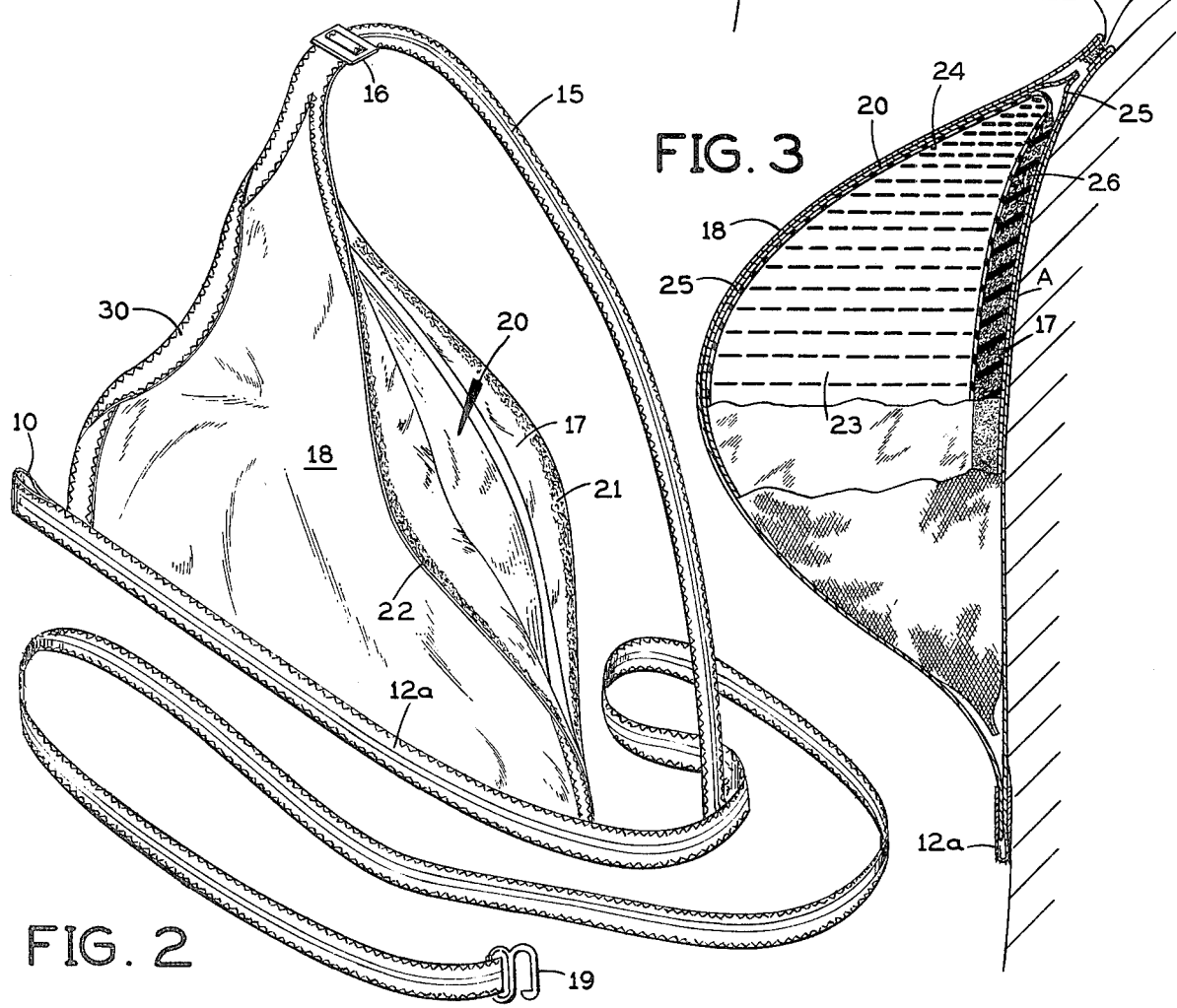
FIG. 2
FIG. 3

BREAST FORM HOLDER

BACKGROUND OF THE INVENTION

Various arrangements have been proposed heretofore to compensate for the surgical removal of one or both of a woman's breasts. Examples of such prior arrangements are disclosed in the following U.S. Pat. Nos.: Williams 3,950,792; Mailleue 1,417,930; and Pittman 3,401,407.

In addition, breast forms have been used which stimulate a woman's natural unamputated breast and which may be inserted in a conventional bra to fill it out to the contours of the natural breast. However, when the bra is removed the breast form is very likely to fall out.

Also, conventional bras have been designed with pockets for receiving breast forms.

SUMMARY OF THE INVENTION

The present invention is directed to a novel breast form holder which is to be worn over a woman's amputated breast and which provides a pocket into which a breast form of known design may be inserted and from which that breast form may be removed, when desired.

In accordance with this invention, a breast form holder is provided which has back and front panels shaped and dimensioned to cover the entire surgical area of an amputated woman's breast and permanently attached to each other over their respective peripheries except at one edge. There, the panels are fastened together by manually separable fastener means, such as adhering fabric, which may be separated to provide an opening leading into a pocket between the panels for receiving a breast form of known design. The front panel of the present breast form holder is of then, soft, stretchable fabric so that when the filled breast form is in place in the pocket the appearance of an unsupported natural breast is closely simulated when the wearer is at rest or in motion.

Preferably, the present breast form holder also has an adjustable shoulder strap and a body band to extend across the wearer's back and in front.

The invention is embodied in a breast form holder for simulating a single amputated breast.

The principal object of this invention is to provide for a woman with an amputated breast a novel garment for covering the surgically disfigured area and for receiving an artificial breast form to simulate closely an unsupported natural breast. A conventional bra can be worn over the present breast form holder or not, depending upon the wearer's preference or the nature of the wearer's activity at the time, such as when wearing a swim suit or sleepwear. Upon removal of the conventional bra, the filled breast form holder can remain in place while the other, natural breast is exposed. Further objects and advantages of the invention will be apparent from the following detailed description of a presently-preferred embodiment thereof, shown in the accompanying drawings in which:

FIG. 1 is a perspective view of a single breast form holder in accordance with the present invention, worn by a woman with one breast amputated and the other a normal breast;

FIG. 2 is a perspective view of this breast form holder with its form-receiving pocket open; and FIG. 3 is a cross-section taken along the line 3—3 in FIG. 1.

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

Referring first to FIG. 1, the present breast form holder 11 is generally three-sided in outline, with a downwardly curved bottom side 12, an outer side 13 which is inclined upward and laterally inward from the outer end of the bottom side 12, and an inner side 14 which is inclined upward and laterally inward from the inner end of the bottom side 12. The outer and inner sides 13 and 14 are joined to each other at the lower end of a shoulder strap 15 of conventional design which includes a length adjusting slide 16.

Between the three sides 12, 13 and 14 the breast form holder presents a flexible back panel 17 (FIGS. 2 and 3) of soft fabric which directly overlies the wearer's amputated breast A, as shown in FIG. 3. Also, between the three sides 12, 13 and 14 the breast form holder presents a flexible front panel 18, also preferably of soft fabric, which extends in front of the back panel. The front panel 18 preferably is of thin, knitted tricot, "Spandex" or jersey fabric capable of stretching so that the front panel 18 can bulge out away from the back panel when an insert is placed between them.

Preferably, the two panels 17 and 18 are identical so that the breast form holder can be worn reversibly, i.e., with the panel 17 serving as the front panel when the amputated breast is on the woman's right side rather than the left side as in FIG. 1. The raw edges of the garment may be covered with elastic lace or other suitable material as at 30 which makes the garment reversible.

The front and back panels 17 and 18 are permanently stitched to each other and to a lower body band 12a running along the bottom side 12 below the amputated breast and across the wearer's back and around the opposite side and beneath the other breast. The lower band 12a carries a hook 19 at one end (FIG. 2) for attaching it to a loop 10 on its opposite end between the breasts, as shown in FIG. 1. The lower end of the shoulder strap 15 is stitched to the body band 12 at the back.

The front and back panels 17 and 18 also are permanently stitched to each other and to a band 14a running along the inner side 14. The permanent stitching along these two sides 12 and 14 closes these two sides of a breast-form receiving pocket 20 (FIG. 2) between the front and back panels 17 and 18.

At the remaining side 13 these panels carry confronting strips 21 and 22 of "Velcro" or other adhering fabric which present a multiciplicity of interlocking elements for holding them together after they have been pressed against each other. The adhering fabric strips provide a manually separable fastener means enabling the pocket between the back and front panels 17 and 18 to be opened along the side 13 for inserting a breast form into the pocket and then closed to retain the breast form holder in the pocket. Preferably, the pocket opening at 13 should be about four inches long and the adhering strips 21, 22 should be at least two inches long at this opening.

It is to be understood that a different type of manually separable fastener arrangement, such as snap fasteners, may be provided in place of the adhering fabric strips, if desired.

The side bands 13 and 14 preferably are of elastic fabric which is stretched where it is stitched to the front and back panels 17 and 18 so as to have a snug fit over the wearer.

The breast form itself may be of known design, the details of which are not part of the present invention. As shown in FIG. 3, the breast form has a suitable filler 23 enclosed in a rubber envelope 24 which, in turn, is enclosed in a fabric cover 25, with a pad of foam rubber 26 engaged between the fabric cover 25 and the rubber envelope 24 at the back. The breast form 23–26 when inserted in the pocket 20 of the present breast form holder 11 simulates the contours of a natural, unamputated woman's breast and it has a snug, but slidable, fit between the back panel 17 and the front panel 18 of the present breast form holder when they are held together along the outer edge 13 by the adhering fabric strips 21, 22 interlocking with each other as shown in FIG. 3.

The thin, soft, stretchable fabric in the outer panel 18 of the breast form holder causes it to closely simulate the appearance of an unsupported natural breast when the breast form 23–26 is in the pocket 20 and the form holder is worn over the woman's amputated breast. Consequently, it enhances the woman's appearance and it buoys her self-confidence after a mastectomy, particularly when her dress or blouse is removed in the presence of another person.

The front and back panels 17 and 18 are designed to completely cover the entire surgical area of the amputated breast.

As shown in FIG. 1, the present breast form holder may be worn without a conventional bra covering either it or the other breast, such as when nudity is desired by the wearer or she is wearing a swim suit or a nightgown, for example. In such cases, the filled breast form holder closely simulates in appearance the unsupported natural breast and thereby minimizes the wearer's natural tendency to be self-conscious about her mastectomy.

Alternatively, in other circumstances, such as when the wearer is fully clothed, a conventional bra may be worn covering both the natural breast and the filled breast form holder.

I claim:

1. A self-contained single breast form holder to be worn either with or without a separate brassiere by a woman with an amputated breast, said holder comprising:

a flexible back panel of soft, thin, stretchable material shaped and dimensioned to overlie the wearer's amputated breast;

a flexible front panel of soft, thin, stretchable material extending completely across the front of said back panel;

said back and front panels being shaped and dimensioned to cover the surgically disfigured area of a woman's amputated breast;

each of said panels being substantially three-sided presenting a bottom side, an outer side which is inclined upward and laterally inward from the outer end of said bottom side, and an inner side which is inclined upward and laterally outward from the inner end of said bottom side and is joined to the outer side at the top of the panel;

stitching securing said panels to each other along their bottom and inner sides; manually separable fastener means acting between said panels along their outer sides to releasably attach them together thereat;

said panels being separate from each other except at said stitching and said manually separable fastener means, whereby to form a pocket between them for receiving a woman's breast form inserted between them when last-mentioned fastener means is separated to provide an opening leading into said pocket;

a body band fastened to said panels along their bottom edges, said body band extending beyond said outer sides of the panels and providing an elongated flexible strap adapted to extend across the wearer's back and around the opposite side of the wearer and beneath her other breast;

manually separable fastener means on the opposite ends of said body band for releasable attachment to each other below and between the wearer's breasts;

and a shoulder strap extending from the juncture between said outer and inner sides at the top of the panels down to said body band beyond said outer sides of the panels, whereby to overlie the wearer's shoulder at the side where the amputated breast is located;

said shoulder strap and said body band together positioning the breast form holder on the wearer independent of any brassiere or other garment she may be wearing.

2. A breast form holder according to claim 1, and further comprising stretched elastic bands stitched to said panels along said outer and inner sides of the panels for a snug fit on the wearer thereat.

3. A breast form holder according to claim 2, wherein said front and back panels are substantially identical for reversible wearing of the breast form holder over an amputated breast on either side of the wearer.

4. A breast form holder according to claim 1, wherein said front and back panels are substantially identical for reversible wearing of the breast form holder over an amputated breast on either side of the wearer.

* * * * *